United States Patent
Ikushima et al.

(10) Patent No.: US 6,300,523 B1
(45) Date of Patent: Oct. 9, 2001

(54) NONCATALYTIC ORGANIC SYNTHESIS USING SUPERCRITICAL WATER

(75) Inventors: Yutaka Ikushima; Osamu Sato, both of Miyagi (JP)

(73) Assignee: Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/427,761

(22) Filed: Oct. 27, 1999

(30) Foreign Application Priority Data

Oct. 30, 1998 (JP) .................................................. 10-326190

(51) Int. Cl.$^7$ .................................................. C07C 45/00
(52) U.S. Cl. ........................ 568/383; 568/384; 568/403; 210/762; 210/763; 210/908
(58) Field of Search ..................................... 568/383, 386, 568/403; 423/659; 210/762, 763, 908

(56) References Cited

U.S. PATENT DOCUMENTS

| | | | |
|---|---|---|---|
| 5,565,616 | * 10/1996 | Li et al. ................................ | 585/700 |
| 5,571,423 | * 11/1996 | Daman .................................. | 210/761 |
| 6,010,632 | * 1/2000 | Ross et al. ............................ | 210/759 |

OTHER PUBLICATIONS

Yutaka Ikushima, et al., The Chemical Society of Japan, Chemistry Letters, pp. 109–112, "Solvent Effects on an Enzymatic Ester Synthesis in Supercritical Carbon Dioxide", 1993.

Kiyotaka Hatakeda, et al., The Chemical Society of Japan, Chemistry Letters, pp. 245–246, "Supercritical Water Oxidation of a PCB of 3–Chlorobiphenyl Using Hydrogen Peroxide", 1997.

Yutaka Ikushima, et al., American Chemical Society, J. Phys. Chem., vol. 102, pp. 3029–3035, "Raman Spectral Studies of Aqueous Zinc Nitrate Solution at High Temperatures and at a High Pressure of 30 MPa", 1998.

* cited by examiner

*Primary Examiner*—Sreeni Padmanabhan
(74) *Attorney, Agent, or Firm*—Oblon, Spivak, McClelland, Maier & Neustadt, P.C.

(57) ABSTRACT

This invention is intended to provide a method for producing pinacoline by means of pinacol rearrangement in supercritical water, which affords an extremely high reaction rate without the addition of high concentrations of acid, and this invention is directed to a method for increasing the reaction rate during organic synthesis by utilizing the supply of protons from water under noncatalytic conditions in supercritical water, a method of pinacol rearrangement comprising the production of pinacoline by pinacol rearrangement under noncatalytic conditions without the addition of an acid catalyst in supercritical water, and a method of synthesis comprising the production of cyclic compounds from pinacol under noncatalytic conditions without the addition of an acid catalyst around the critical point (375 to 380° C., 22.5 to 25 MPa) in supercritical water.

4 Claims, 3 Drawing Sheets

NONCATALYTIC ORGANIC SYNTHESIS USING SUPERCRITICAL WATER

BACKGROUND OF THE INVENTION

Disclosure of the Invention

The present invention relates to a novel method of organic synthesis using supercritical water which allows organic synthesis to be carried out at a high reaction rate under noncatalytic conditions without the addition of high concentrations of acid to the supercritical water, and more particularly, this invention relates to a method for carrying out organic synthesis utilizing proton supply from water under noncatalytic conditions in supercritical water, a method for increasing the reaction rate during such organic synthesis, a method of pinacol rearrangement in which pinacoline is produced by pinacol rearrangement under noncatalytic conditions without the addition of an acid catalyst in supercritical water, and a method of cyclization for producing cyclic compounds from pinacol under non-catalytic conditions without the addition of an acid catalyst around the supercritical point.

Background of the Invention

Dramatic changes in the reaction rate and selectivity around the critical point of supercritical fluids in organic chemical reactions using supercritical fluids as the reaction medium have recently been reported (1 to 3: numbers of references described in the last paragraph of this specification; and so forth on) and have become the focus of considerable attention. Supercritical fluids have physical properties being intermediate between liquids and gases, with molecular motion energy that is always greater than the intermolecular force. Nevertheless, because of conflict between the formation of the system order due to intermolecular force and the scattering of molecules due to kinetic energy thereof, the molecules are violently reversed while the order is preserved (cluster formation) to some extent at the microscopic level. Thus, slight changes in temperature and pressure around the critical point result in significant changes in fluid density.

Examination of the reaction molecules in organic reactions featuring the use of such supercritical fluids as the reaction medium has revealed that the chemical interaction between different species of molecules in minute surrounding areas thereof changes in particular around the critical point (4 and 5). Changes in the dynamic and static structures are assumed to considerably affect the reaction equilibrium and rate, and the product distribution.

The inventors thus developed methods of in situ measurement such as high pressure FT-IR, UV/Vis, and Raman spectroscopy, which have been used to achieve an understanding, at the molecular level, of the relationship between the reaction site at the microscopic level and factors affecting reactivity. This has resulted not only in the elucidation of the relationship between reactivity and the function of supercritical fluids as the reaction site, but has also allowed the microscopic site of reaction formed in supercritical fluids to be controlled by the manipulation of temperature and pressure at the microscopic level, potentially leading to the development of a novel, industrially promising chemical reaction process with high selectivity and high efficiency.

In anticipation of the application of such supercritical fluids in reaction sites, attention has recently focused on chemical reactions in which supercritical water serves as the reaction site as same as supercritical carbon dioxide. Carbon dioxide is nonpolar in a supercritical state and has essentially the same properties, whereas water in a supercritical state is known to have completely different properties than water at normal temperature. For example, permittivity of water at ordinary temperature and atmospheric pressure is about 80, whereas the permittivity of supercritical water is about 3 to 20 around the critical point, allowing the permittivity of water to be continuously controlled within a wide range by temperature and pressure. It is thus possible that organic compounds with low polarity such as aromatic compounds and various gases can be dissolved in supercritical water, which would be extremely valuable for industrial purposes.

The supercritical water oxidation (SCWO) of toxic substances through the exploitation of the properties of supercritical water is thus receiving attention all over the world (6). This is because of the possibility that many toxic organic substances (such as chlorine-containing aromatic compounds), oxidizing agents such as air, oxygen and other might be readily dissolved in supercritical water and they might be decomposed by oxidation (combustion). The inventors have succeeded in the complete decomposition of polychlorinated biphenyl (PCB) by means of SCWO using hydrogen peroxide as oxidating agent (7). Supercritical water has wide-ranging possibilities in applications as reaction media in thermochemical reactions such as dehydration reactions, pyrrolysis, reduction, and synthesis, showing the promise of supercritical water as a reaction solvent.

Although organic synthesis in supercritical fluids has been noted, most examples have been chemical reactions featuring the use of organometal catalysts in supercritical carbon dioxide (8), with very few examples of organic synthesis using supercritical water as the reaction site. The study of organic synthesis in supercritical water is extremely significant because nonpolar compounds can be readily dissolved in supercritical water, with a far higher critical temperature than that of carbon dioxide.

Recent research (9, 10) has revealed that water has extremely weak hydrogen bonding strength around the critical point of water, and has a dimer or monomer structure. Research (11, 12) by the inventors on supercritical water or high-temperature and high pressure aqueous solutions using Raman spectroscopy showed a strong possibility that the structural instability (change of dynamics) around the critical point resulted in the further break down of the monomer structure and production of proton. If there are few site at which protons can be held within the system following the production thereof, the local proton concentration could be increased, which should also affect the chemical reactivity.

As noted above, much research has thus far been undertaken on the temperature and pressure dependency of the reaction rate and selectivity in organic chemical reactions in supercritical fluids (such as carbon dioxide, water, ethane, propane and the like) from the standpoint of the solvent or solute clustering effects or the physicochemical properties of solvents, centering around the critical point. There has also been considerable research on various chemical reactions in supercritical fluids in the presence of catalysts, the development of spectroscopic methods of measurement in high temperature and high pressure reactions in supercritical water, and the possibility of devising a novel chemical reaction comprising such an inorganic reaction. If the relationship between the micro factors in the vicinity of the substrate molecules and the chemical reactivity in supercritical fluids could be elucidated on a molecular scale, the reactivity and function of the reaction site in supercritical states could be elucidated, and a reaction process with higher selectivity and a higher reaction rate could be devised, which could be extremely useful for both scientific and industrial purposes. However, thus far, there have been virtually no reports on achieving a high reaction rate utilizing the supply of protons from water during organic synthesis in supercritical water.

SUMMARY OF THE INVENTION

The present invention is intended to provide a method for producing pinacoline by means of pinacol rearrangement in supercritical water, which affords an extremely high reaction rate without the addition of high concentrations of acid.

The present invention is directed to a method for increasing the reaction rate during organic synthesis by utilizing the supply of protons from water under noncatalytic conditions in supercritical water, a method of pinacol rearrangement comprising the production of pinacoline by pinacol rearrangement under noncatalytic conditions without the addition of an acid catalyst in supercritical water, and a method of synthesis comprising the production of cyclic compounds from pinacol under noncatalytic conditions without the addition of an acid catalyst around the critical point (375 to 380° C., 22.5 to 25 MPa) in supercritical water.

DETAILED DESCRIPTION OF THE INVENTION

With the foregoing in view, the inventors confirmed that the Beckman rearrangement reaction proceeded under noncatalytic conditions in supercritical water, and they conducted in situ observations and studied the possibilities of noncatalytic pinacol rearrangement in supercritical water. As a result, it was discovered that the reaction rate could be increased in organic synthesis utilizing the proton supply from water under noncatalytic conditions in supercritical water, that an extremely high velocity constant could be obtained by means of pinacol rearrangement in supercritical water, and that cyclic compounds are specifically produced in addition to pinacoline around the critical point (375 to 380° C., 22.5 to 25 MPa). The present invention was perfected upon the finding that cyclic compounds are produced from pinacol.

That is, an object of the present invention is to provide a method of organic synthesis utilizing the supply of protons from water under noncatalytic conditions in supercritical water, and to provide a method for increasing the reaction rate during such organic synthesis.

Another object of the present invention is to provide a method of pinacol rearrangement comprising the production of pinacoline by means of pinacol rearrangement under noncatalytic conditions without the addition of an acid catalyst in supercritical water, and to provide a method for the novel production of cyclic compounds from pinacol around the critical point.

To solve the aforementioned drawbacks, the present invention comprises the following technical means:

(1) A method of noncatalytic organic synthesis, comprising carrying out an organic reaction by utilizing protons supplied from water under noncatalytic conditions without the addition of an acid catalyst in supercritical water.

(2) A method for increasing the reaction rate in organic synthesis by utilizing protons supplied from water under noncatalytic conditions without the addition of an acid catalyst in supercritical water.

(3) A method of pinacol rearrangement, comprising performing pinacol rearrangement under noncatalytic conditions without the addition of an acid catalyst to produce pinacoline in supercritical water.

(4) A method of cyclization, comprising cyclizing pinacol under noncatalytic conditions without the addition of an acid catalyst to produce cyclic compounds around the critical point (375–380° C., 22.5–25 Mpa) in supercritical water.

The present invention is described in further detail below.

As a result of the confirmation that the Beckman rearrangement reaction proceeds without a catalyst in supercritical water, as well as further research on the possibility of pinacol rearrangement in supercritical water, the inventors have discovered that pinacoline is produced under noncatalytic conditions without the addition of an acid catalyst, and that the reaction rate can be increased in organic synthesis by means of the proton supply from water. Conventional pinacol rearrangement does not proceed without the addition of an acid such as sulfuric acid, hydrochloric acid or the like as a catalyst, so perchloric acid or hydrochloric acid, for example, is added in high concentrations. It has been known that the reaction velocity constant increases as the acid concentration increases, resulting in a reaction that is promoted by the acid, in other words, by protons produced from the acid. It has been also known that cyclic compounds are produced from pinacol.

In their previous research on the structure of supercritical water (water with a critical temperature of 375° C. and a critical pressure of 22.05 Mpa or more) using high-temperature and high-pressure Raman spectroscopy, the inventors have discovered that the hydrogen bonding structure broke down considerably around the critical point. Because it was not confirmed until now that the hydrogen bonding structure of water broke down as far as protons, the inventors were the first to propose a reaction involving protons in supercritical water to verify this, and they then attempted pinacol rearrangement to further confirm the supply of protons from water on the assumption that there was a significant possibility of protons being supplied from supercritical water.

As a result, the inventors have found that the reaction rate in organic synthesis can be increased by the supply of protons from water in supercritical water, and that pinacoline can be produced at a high reaction rate by pinacol rearrangement under noncatalytic conditions without the addition of an acid catalyst in supercritical water. As will be shown in the examples below, the dramatic increase in the velocity constant as a result of pinacol rearrangement in supercritical water was completely unexpected. It has been also confirmed by NMR and GC-MS in addition to IR that pinacoline is the only product except around the critical point.

The inventors also have found that the dehydration mechanism of pinacol around the critical point of supercritical water is unlike that of the aforementioned pinacol rearrangement, that dienes with covalent double bonds are produced, that the Diels-Alder reaction occurrs between the diene compounds which are produced, and that new cyclic compounds are produced. Pinacol rearrangement proceeds in the presence of strong acids such as sulfuric acid and hydrochloric acid, whereas the dehydration of pinacol to dienes proceeds in the presence of weak acids such as boron chloride (13), so there is a possibility that the acid strength in supercritical water changes depending on temperature and pressure, results which were completely unexpected. Products were verified by GC-MS and NMR.

Because the aforementioned rearrangement reaction proceeds in a supercritical state, the temperature is high (in terms of equipment, it is difficult to carry out the reaction at elevated temperature while adding high concentrations of acid, and even if it were possible to do so, it is assumed that the properties of the acid would change a great deal), but with the increasing concern recently over environmental problems, it could be quite significant to obtain an extremely high reaction rate without the addition of high concentrations of acid which adversely affect the environment. Since new cyclic compounds are produced by a dehydration mechanism that is different from pinacol rearrangement around the critical point of supercritical water, it is possible that acid strength could be modified simply by temperature and pressure in supercritical water, which would be important from a scientific and industrial standpoint. The aforementioned rearrangement reaction would also be better for the environment because the solvent used in the reaction would just be inexpensive water, with no need to use organic solvents.

It may be seen in the present invention that a high reaction rate can be obtained by means of organic synthesis utilizing the supply of protons from water under noncatalytic conditions without the addition of high concentrations of acid in supercritical water.

It may also be seen that the velocity constant increases greatly in pinacol rearrangement in supercritical water.

It may furthermore be seen that new cyclic compounds are produced around the critical point of supercritical water.

The inventors were thus the first to show the effectiveness of a method for carrying out organic synthesis utilizing the supply of protons from water under noncatalytic conditions without the addition of an acid catalyst in the aforementioned supercritical water, a method for increasing the reaction rate during organic synthesis, and the like. The present invention is thus not limited to a single specific method. Any method featuring the use of these methods, no matter what type, belongs to the methods of the present invention.

Chemical Formula 1

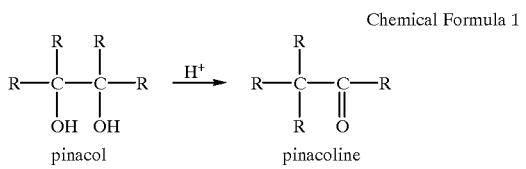

R:CH$_3$

Explanation of Symbols:
1) main unit (Hastelloy C-276)
2) main unit fixing diamond window
3) molybdenum for setting diamond window
4) diamond window

BEST MODE FOR CARRYING OUT THE INVENTION

The present invention is described in detail below based on embodiments, but the following embodiments are intended to show preferred examples of the present invention, and do not in any way limit the present invention.

EXAMPLE 1

(1) Overview of System

Figure 3:
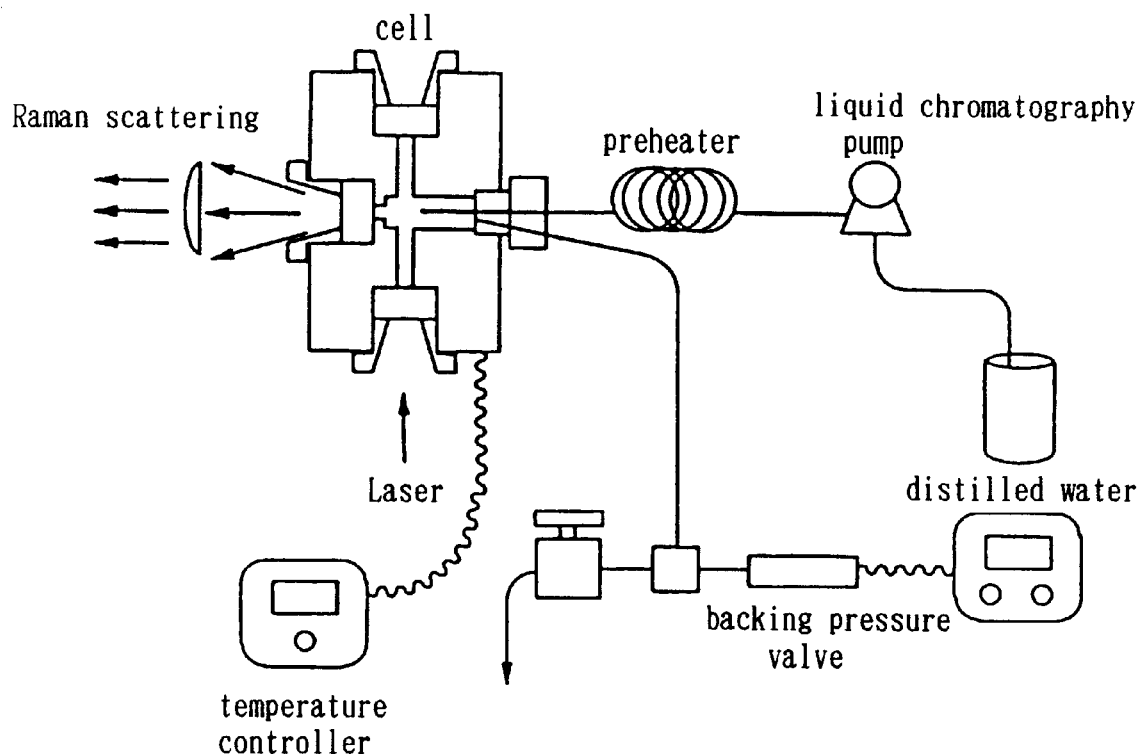
FIG. 3 is a schematic of a flow-through type of high-temperature, high-pressure laser Raman spectroscopic system.

FIG. 3 is a schematic of the flow type of high-temperature, high-pressure laser Raman spectroscopic system used in the present embodiment. Measurements are carried out by degassing high purity distilled water (distilled three times) based on thorough nitrogen gas bubbling, filtering the water, and continuously pumping the water using a common high performance liquid chromatography pump. The pressure was controlled to a precision of within ±0.1 MPa by a backing pressure valve, and the temperature was controlled by the temperature controller of a mantle type of heating tower. The temperature was calibrated by measuring the pressure at an arbitrary temperature (such as 350° C.) in double phase regions where gas and liquid coexisted, and comparing the known temperature at the saturation point with reference to an NBC/NRC Table.

(2) Test Methodology

1) High-Temperature, High-Pressure Cell

Figure 1:
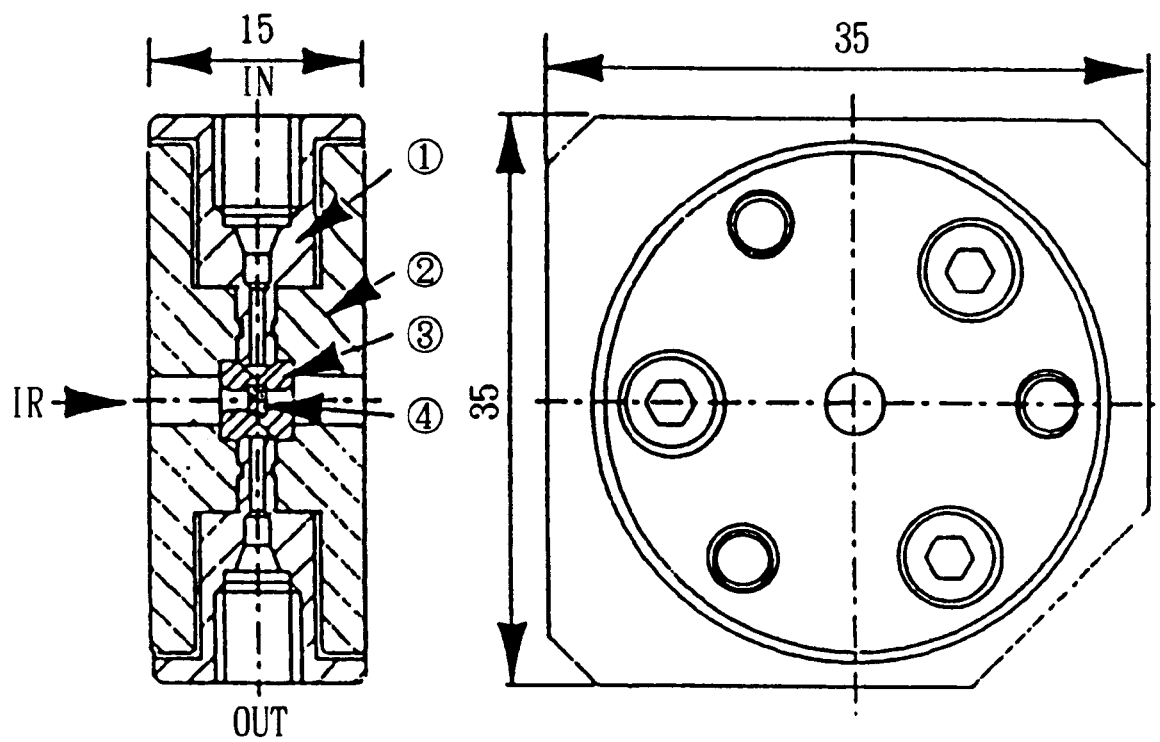
FIG. 1 is a schematic of a high-temperature, high-pressure cell.

The flow type of high-temperature, high-pressure FTIR system devised by the inventors is capable of continuous reaction in supercritical water and in situ observation by IR. FIG. 1 is a schematic of the high-temperature, high-pressure cell. The use of diamond for the window allows measurement within the common IR range. The cell optical path length was adjusted by using a metal foil space inserted between the diamond window and a buffer member. The optical path length was measured on the basis of water refractive index and interference fringes. Although unaffected by pressure, the optical path length increased with temperature, reaching 24.4 $\mu$m at 100° C., 44.0 $\mu$m at 400° C., and becoming constant beyond 400° C. The volume of the reaction component (sum of volumes of tubing in heating tower and routes including optical path inside cell) was 0.662 mL.

2) Method

High purity distilled water thoroughly degassed with He was used to prepare an aqueous solution of pinacol {(CH$_3$)$_2$(OH)C(OH)(CH$_3$)$_2$}, and the concentration thereof was adjusted to a molality of 0.422. Water or pinacol aqueous solution was continuously pumped by a liquid chromatography pump. The pressure was controlled to a precision of within ±0.1 MPa by a backing pressure valve, and the temperature was controlled to a precision of within ±0.2° C. by the temperature controller of a mantle type of vacuum heating tower. Reactions were carried out at temperatures from room temperature to 748K, pressures from 0.1 to 35 MPa, and residence time from 120 to 8 seconds. The IR spectra of the reaction solution were taken at a resolving power of 4 cm$^{-1}$ in 50 calculations (1.2 second/scan) after the predetermined pressure and temperature had been reached and after equilibrium thereof had been reached at a constant flow rate.

(3) Results 1

Figure 2:
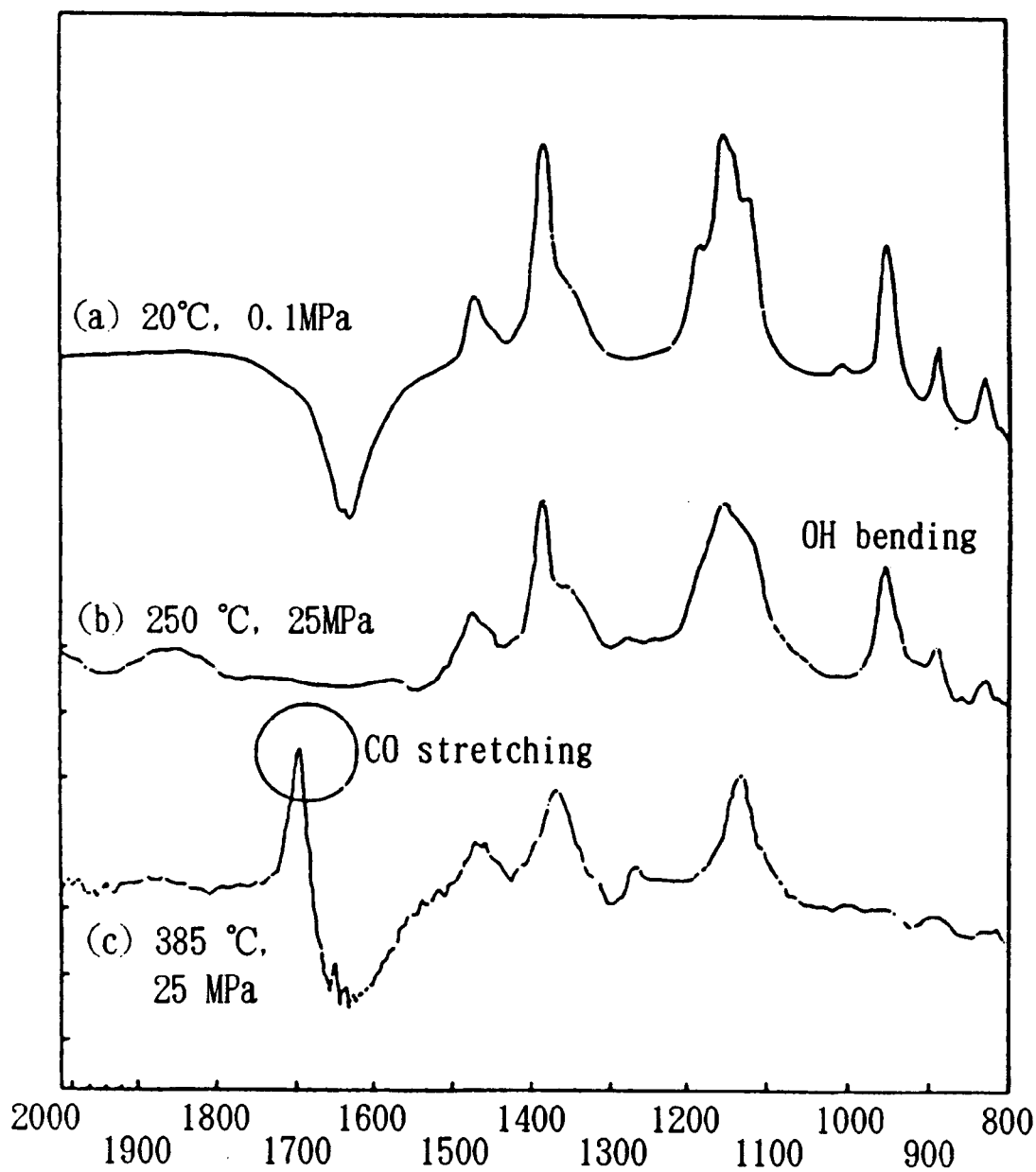
FIG. 2 shows IR spectra for pinacol aqueous solution at 2000 to 800 cm$^{-1}$.

FIG. 2 shows the IR spectra of the pinacol aqueous solution at 2000 to 800 cm$^{-1}$ as measured at a constant residence time of 108 seconds and at a pressure and temperature of 0.1 MPa and 20° C. (a), 25 MPa and 250°C. (b), and 25 MPa and 38.5° C. (c). All results were amended with the background spectra of pure water measured under the same conditions. The greatest changes in the figure were that the absorption peaks at 945 cm$^{-1}$ of (a) and (b) were disappeared, and powerful absorption at 1700 cm$^{-1}$ was appeared at (c).

It is clear that new substances were specifically produced under the conditions of (c). Since 945 cm$^{-1}$ indicates alcohol OH bending, and 1700 cm$^{-1}$ indicates C=O stretching of typical aliphatic ketones, it was concluded that pinacol rearrangement had taken place, and that pinacoline had been {(CH$_3$)$_3$CCOCH$_3$} produced. Its production was verified by GC-MS and NMR.

The results revealed for the first time that pinacol rearrangement proceeded without a catalyst in supercritical water, and that protons were produced from supercritical water itself.

(4) Results 2

The test conditions and the velocity constant obtained in the present invention are given below. The velocity constant was treated as a first order parameter in the same manner as in other literatures, and was calculated on the basis of the reduction rate in characteristic absorption wave number (OH bending) for pinacoline at varying temperatures, pressures, and residence times of pinacoline aqueous solution using the flow type of high-temperature, high-pressure FTIR device developed by the inventors. No pinacoline was produced at any pressure when the temperature was lower than 250° C.

1) Test Conditions

Pinacol aqueous solution concentration: 0.4 M
Temperature: 20 to 450° C.
Pressure: 0.1, 20, 22.05, 25, 30, 35 MPa
Residence time; 50 to 120 seconds
The type of pinacol used was R=CH$_3$.

2) Results

| Temperature (° C.) | Velocity constant (S$^{-1}$) |
|---|---|
| (pressure of 25 MPa) | |
| 300 | 1.26 × 10$^{-1}$ |
| 350 | 2.37 × 10$^{-1}$ |
| 370 | 3.41 × 10$^{-1}$ |
| 385 | 3.58 × 10$^{-1}$ |
| 395 | 5.41 × 10$^{-1}$ |
| 400 | 5.66 × 10$^{-1}$ |
| 425 | 1.32 |
| 450 | 1.96 |
| (pressure of 30 MPa) | |
| 300 | 1.26 × 10$^{-1}$ |
| 350 | 3.38 × 10$^{-1}$ |
| 370 | 4.52 × 10$^{-1}$ |
| 385 | 4.55 × 10$^{-1}$ |
| 395 | 7.36 × 10$^{-1}$ |
| 410 | 8.07 × 10$^{-1}$ |
| 430 | 1.73 |
| (pressure of 35 MPa) | |
| 300 | 3.56 × 10$^{-1}$ |
| 370 | 3.43 × 10$^{-1}$ |
| 385 | 3.58 × 10$^{-1}$ |
| 395 | 4.52 × 10$^{-1}$ |
| 425 | 0.87 × 10$^{-1}$ |
| 450 | 1.45 |

Although there was some variation depending on the acid concentration and temperature in the results being compared, the velocity constant had increased nearly 600-fold compared to that in conventional methods (HClO$_4$:0.71 M; temperature: 113.5° C.). Although the same reaction has been carried out using 0.871 M hydrochloric acid catalyst at high pressure as in the present invention in the conventional literature (The Review of Physical Chemistry of Japan, Vol. 40, No. 1 (1970)), comparison of the best research results by the inventors with the aforementioned case in the conventional literature, where the pressure was 46.7 MPa and the temperature was 70° C., reveals a 1.5×10$^5$ fold increase in the case.

(5) Results 3

Table 1 shows the products synthesized from pinacol {(CH$_3$)$_2$(OH)C(OH)(CH$_3$)$_2$} and their selectivity without a catalyst in supercritical water. The production of pinacoline {(CH$_3$)COC(CH$_3$)$_3$} and 1,2,5-trimethyl-5-isopropenyl-1-cyclohexene given as products in Table 1 was confirmed by GC-MS and NMR. The selectivity for 1,2,5-trimethyl-5-isopropenyl-1-cyclohexene was about 20%, but it was produced specifically only around the critical point. Pinacoline was produced in a ratio of 100% under other conditions. The test conditions were the same as those for Results 2.

TABLE 1

| | product distribution | |
|---|---|---|
| conditions | (pinacoline structure) (%) | (cyclohexene structure) (%) |
| 375~380° C. 22.05~25 MPa | 77% | 23% |
| in supercritical water with condition other than the above | 100% | 0% |

Virtually no examples of such synthesis in supercritical water have been reported in research anywhere in the world. The Diels-Alder is the only reaction to occur to a certain extent in supercritical water in any research other than that by the inventors.

There are a number of reports on decomposition in supercritical water.

INDUSTRIAL APPLICABILITY

As described above, the present invention relates to a method for increasing the reaction rate during organic synthesis by utilizing the supply of protons from water under noncatalytic conditions without the addition of an acid catalyst in supercritical water, a method for producing pinacoline by pinacol rearrangement, and a method for producing cyclic compounds from pinacol around the critical point. Particular advantages of the present invention are that:

(1) pinacoline can be produced under noncatalytic conditions without the addition of an acid catalyst;
(2) the velocity constant can be dramatically increased by means of pinacol rearrangement in supercritical water;
(3) an extremely high reaction rate can be obtained without adding high concentrations of acid;
(4) pinacol rearrangement is promoted under noncatalytic conditions without the addition of an acid catalyst in supercritical water;
(5) new cyclic compounds can be synthesized by exploiting the changes in acid strength in supercritical water around the critical point of supercritical water;
(6) organic synthesis can be carried out by utilizing the protons supplied from supercritical water; and
(7) a better method synthesis for the environment without using high concentrations of acid or organic solvents can be provided.

The following are references.

1. J. B. Ellington, J. F. Brennecke, J. Chem., Soc. Chem. Commun., 1094 (1993)

2. Y. Ikushima, N. Saito, T. Yokoyama, K. Hatakeda, S. Ito, M. Arai, H. W. Blanch, Chem. Lett, 108 (1993)
3. P. G. Jessop, T. Ikariya, R. Noyori, Science, 269, 1065 (1995)
4. Y. P. Sun, M. A. Fox, K. P. Johnston, J. Am. Chem. Soc., 114, 1187 (1992)
5. A. A. Chialvo, P. G. Debenedetti, Ind. Eng. Chem. Res., 31, 1391 (1992)
6. E. T. Ryan, T. Xiang, K. P. Johnston, M. A. Fox, J. Phys. Chem., 100 9365 (1996)
7. K. Hatakeda, Y. Ikushima, S. Ito, O. Sato, N. Saito, Chem. Lett., 245 (1997)
8. M. J. Burk, S. Feng, M. F. Gross, W. Tumas, J. Am. Chem. Soc., 117, 8277 (1995)
9. N. Matsubayashi, C. Wakui, M. Nakahara, Phys. Rev. Lett., 78, 2573 (1997)
10. M. M. Hoffmann, S. Conradi, J. Am. Chem. Soc., 119, 3811 (1997)
11. Y. Ikushima, K. Hatakeda, N. Saito, M. Arai, J. Chem. Phys., 108, 5855 (1998)
12. Y. kushima, N. Saito, M. Arai, J. Phys. Chem. B, 102, 3029 (1998)
13. C. F. R. Allen, A. Bell, Org. Syntheses Coll., 3, 312 (1955)

What is claimed is:

1. A method of noncatalytic organic synthesis comprising carrying out an organic reaction in supercritical water by utilizing protons which are supplied from the supercritical water under noncatalytic conditions without adding an acid catalyst to the supercritical water in the absence of oxidant, a heterogeneous agent or other additives.

2. A method for increasing the reaction rate in organic synthesis comprising; carrying out an organic reaction in a supercritical water by utilizing protons which are supplied from the water under noncatalytic conditions without adding an acid catalyst to the supercritical water in the absence of additives.

3. A method of pinacol rearrangement, comprising performing pinacol rearrangement under noncatalytic conditions without the addition of an acid catalyst to produce pinacoline in supercritical water.

4. A method of cyclization, comprising cyclizing pinacol under noncatalytic conditions without the addition of an acid catalyst at 375–380° C., 22.5–25 mPa to produce cyclic compound in supercritical water.

* * * * *